United States Patent
Dass et al.

(10) Patent No.: US 8,519,446 B2
(45) Date of Patent: Aug. 27, 2013

(54) ETCH RESISTANT GAS SENSOR

(75) Inventors: Ronald I. Dass, Austin, TX (US); James Novak, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 1001 days.

(21) Appl. No.: 12/333,545

(22) Filed: Dec. 12, 2008

(65) Prior Publication Data

US 2009/0090170 A1 Apr. 9, 2009

Related U.S. Application Data

(63) Continuation-in-part of application No. 12/201,856, filed on Aug. 29, 2008.

(60) Provisional application No. 60/968,751, filed on Aug. 29, 2007.

(51) Int. Cl.
G01N 27/407 (2006.01)

(52) U.S. Cl.
USPC ...... 257/253; 73/31.05; 73/31.06; 73/335.05; 422/82.01; 422/82.02; 422/82.04; 422/83; 422/98

(58) Field of Classification Search
USPC ............ 73/31.05, 31.06, 335.05; 257/253; 422/82.01, 82.02, 82.04, 83, 98
See application file for complete search history.

(56) References Cited

U.S. PATENT DOCUMENTS

| | | | |
|---|---|---|---|
| 3,575,835 A | 4/1971 | Smith et al. | |
| 3,592,694 A | 7/1971 | Urbach et al. | |
| 5,116,759 A | 5/1992 | Klainer et al. | |
| 5,255,067 A | 10/1993 | Carrabba et al. | |
| 5,344,546 A | 9/1994 | Kiesele et al. | |
| 5,567,622 A | 10/1996 | Jaduszliwer et al. | |
| 5,602,325 A | 2/1997 | McClanahan et al. | |
| 5,610,393 A | 3/1997 | Klimcak et al. | |
| 5,674,751 A | 10/1997 | Jaduszliwer et al. | |
| 5,719,061 A | 2/1998 | Rose-Pehrsson et al. | |
| 5,747,348 A | 5/1998 | Jaduszliwer et al. | |
| 6,111,280 A * | 8/2000 | Gardner et al. | 257/253 |
| 6,202,471 B1 * | 3/2001 | Yadav et al. | 73/31.05 |
| 6,328,932 B1 | 12/2001 | Carter et al. | |
| 6,627,319 B2 | 9/2003 | Jacquiod et al. | |
| 7,053,425 B2 | 5/2006 | Sandvik et al. | |
| 7,080,545 B2 | 7/2006 | Dimeo, Jr. et al. | |

(Continued)

FOREIGN PATENT DOCUMENTS

WO  WO 2004/012234  2/2004

OTHER PUBLICATIONS

Domansky et al., Development and calibration of field-effect transistor-based sensor array for measurement of hydropgen and ammonia gas mixtures in humid air, 1998, American Chemical Society, Anal. Chem. 1998, 70, pp. 473-481.*

Brayner et al. "Hydrazine decomposition over niobium oxynitride with macropores generation," Catalysis Today 57 (2000) pp. 225-229.

Xiaowei Chen et al. "A novel catalyst for hydrazine decomposition: molybdenum carbide supported on γ-Al2O3," Chem. Commun., 2002, pp. 288-289.

(Continued)

*Primary Examiner* — In Suk Bullock
*Assistant Examiner* — Robert Eom
(74) *Attorney, Agent, or Firm* — Kelly Kordzik; Matheson Keys & Kordzik PLLC

(57) ABSTRACT

A gas sensor for sensing chemical gases utilizes a metal oxynitride as the sensing material, which changes its conductivity when exposed to the analyte gas. The change in conductivity is measured for the sensor output. The metal may be either tungsten or molybdenum.

21 Claims, 4 Drawing Sheets

(56) References Cited

U.S. PATENT DOCUMENTS

| | | |
|---|---|---|
| 7,228,724 B2 | 6/2007 | Chen et al. |
| 7,296,458 B2 | 11/2007 | Dimeo, Jr. et al. |
| 7,367,215 B2 | 5/2008 | Monty |
| 2001/0044154 A1 | 11/2001 | Evans |
| 2004/0104129 A1 | 6/2004 | Gu |
| 2004/0163445 A1 | 8/2004 | Dimeo, Jr. et al. |
| 2004/0261500 A1 | 12/2004 | Ng |
| 2005/0005675 A1 | 1/2005 | Monty |
| 2005/0155858 A1 | 7/2005 | Monty |
| 2006/0124448 A1 | 6/2006 | Jayaraman et al. |
| 2006/0270053 A1 | 11/2006 | Tilak et al. |
| 2006/0289351 A1 | 12/2006 | Xiao |
| 2007/0157703 A1 | 7/2007 | Tilak et al. |
| 2007/0166832 A1 | 7/2007 | Tilak et al. |
| 2007/0281160 A1 | 12/2007 | Krishna et al. |

OTHER PUBLICATIONS

International Searching Authority: Notification of Transmittal of the International Search Report and the Written Opinion of the International Searching Authority for International Application No. PCT/US06/30314 (11 pages), mailed Sep. 12, 2008.

Brayner et al., "Hydrazine decomposition over niobium oxynitride with macropores generation," Catalysis Today 57 (2000) pp. 225-229.

ISA/US; International Search Report and the Written Opinion of the International Searching Authority for International Application No. PCT/US06/30314, mailed Sep. 12, 2008, 5 pages.

Chen et al., "A novel catalyst for hydrazine decomposition; molybdenum carbide supported on y-$Al_2O_3$," Chem. Commun., 2002, pp. 288-289.

* cited by examiner

STEP 1) CONTACTS LAYER | PHOTO LITHOGRAPHY DEPOSITION, LIFTOFF

METAL CONTACTS

STEP 2) SENSING LAYER | PHOTO LITHOGRAPHY DEPOSITION, LIFTOFF

SENSING MATERIAL ($MN_XO_4$, $MC_XO_4$, $MC_X$)

STEP 3) POST-DEPOSITION TREATMENT | HEAT, TIME, GAS ATMOSPHERE, ETC.

STRUCTURE TUNED SENSING MATERIAL

ETCH RESISTANT GAS SENSOR

CROSS-REFERENCE TO RELATED APPLICATIONS

This application is a continuation-in-part of U.S. patent application Ser. No. 12/201,856, which claims priority to U.S. Provisional Application Ser. No. 60/968,751, filed on Aug. 29, 2007, the entire contents of which are hereby incorporated by reference herein.

BACKGROUND

Metal oxides are useful for gas sensors. These materials show a change in conductivity when gas analytes are reduced or oxidized at their surface. Basic electrochemistry teaches that when an analyte molecule is oxidized its contact surface is reduced. This surface oxidation (or reduction) of the analyte gas which forms a redox reaction will introduce (or remove) electrons into (or from) the conduction band of the metal oxide. This reaction produces a change in the mobile charge carrier concentration within the oxide and thus a change in its electronic conductivity. The metal oxide conductivity can either increase or decrease and depends on its electronic structure and the particular analyte with which it is reacting.

This reaction usually takes place with an adsorbed oxygen species and/or defect sites within the surface structure of the metal oxide. This allows the sensor to refresh itself in ambient air as oxygen can re-adsorb after a sensing event takes place.

A problem with these metal oxide materials is their susceptibility to damage when very chemically aggressive analytes are present. Manufacturing and industrial process control, environmental monitoring, health and safety, and pollution control each have requirements for gas sensors which can withstand exposure to dangerous and chemically reactive analytes. These analytes might include acids, bases, and particular noxious chemicals. Specific examples are HCl, HF, $NO_x$, $NH_3$, $N_2H_4$, and KOH. These chemicals react with the sensor material surface and remove oxygen or metals from its crystal structure through formation of stable compounds with a high bond strength or kinetics faster than the refresh mechanism. This implies that the metal oxides cannot sense noxious chemicals without suffering irreversible material damage.

In the presence of chemically-reactive, noxious chemicals, metal oxide gas sensors suffer irreversible damage. This damage can manifest itself as the removal (etching) of the metal oxide from the sensor surface. These are the same chemical reactions used in CMOS processing labs to etch wafers and process levels to correct thickness.

Etch resistant layers are commonly found in CMOS processing. These materials might include nitrides such as silicon nitride ($Si_3N_4$). This insulator is commonly used as a passivation layer and dielectric in electronic materials applications. These nitrides would not work for conductimetric (measurement of a change in conductivity) sensing applications due to their electronically insulating nature.

DETAILED DESCRIPTION

Figure 1:
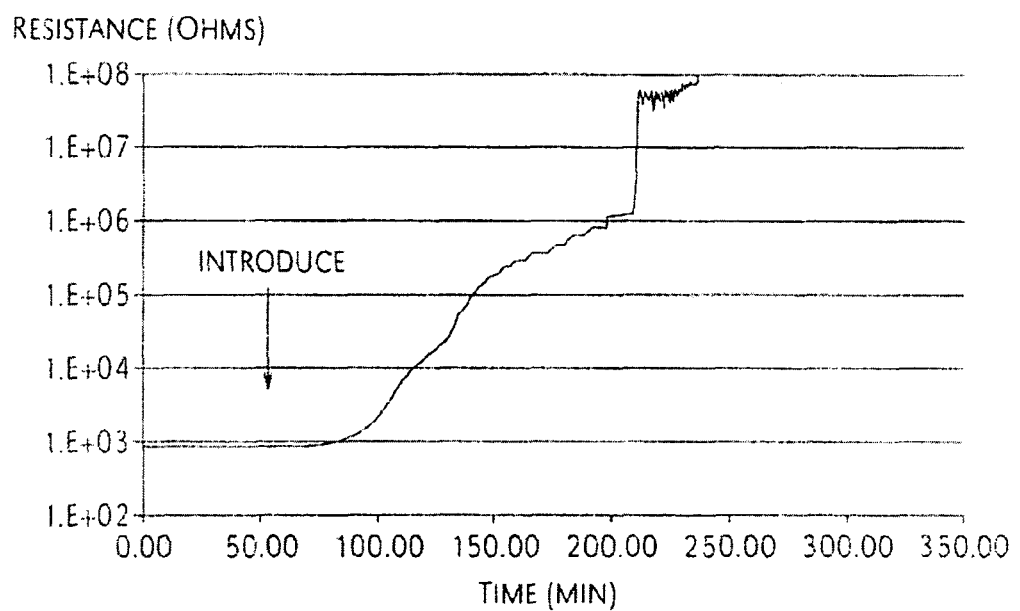
FIG. 1 illustrates a graph of a time-based sensor response to 3 ppm hydrazine. The sharp change in resistance at 210 minutes was due to etch removal of the sensing metal oxide.

A solution to the aforementioned etch problem with metal oxides and the insulating nature of various nitrides is to combine them in a chemistry of metal oxynitrides or nitrides, or metal oxycarbides or carbides. Embodiments of the present invention replace the metal oxide sensing material with a metal nitride, oxynitride, carbide or oxycarbide. The oxynitrides will have a generic stoichiometry of $M_aM_bN_xO_y$. The metal nitrides will have a generic stoichiometry of $M_aN_x$. The oxycarbides will have a generic structure of $M_aM_bC_xO_y$. The metal carbides will have a generic stoichiometry of $M_aC_x$. These systems may have one or more metals and will have a varying stoichiometry of oxygen and nitrogen or oxygen and carbon depending on the valence state of the metal(s) in the crystal lattice structure.

Metal oxynitrides, nitrides, oxycarbides, and carbides have been used as diffusion barriers for large molecules. For example, U.S. patent application publication US 2006/0124448 discloses that an inorganic oxide, nitride, oxynitride or carbide can be used as a hydrogen permeable inorganic layer to allow hydrogen to pass and exclude larger molecules such as carbon monoxide, oxygen, hydrogen sulfide, and sulfur dioxide. These materials are not used as the active material which senses the analyte molecule.

Variation in the process conditions for the material deposition as well as post-deposition treatment enable the baseline electronic conductivity of the metal oxynitride or nitride, or oxycarbide or carbide to be easily tuned. Examples of deposition techniques include electron-beam evaporation, ion gas sputtering, thermal evaporation, pulsed-laser deposition (PLD), and chemical vapor deposition (CVD). Examples of post-deposition treatments include thermal annealing in a vacuum or controlled atmosphere, each of which can be performed with a variable anneal temperature, gas concentration, gas composition, annealing time, and heating and cooling rates. These post-deposition treatments serve to tune the nature of the crystallographic phase or polymorph, surface morphology, compound stoichiometry, and also, the mobile charge carrier concentration. This tenability enables the custom design of a specific sensor for a target analyte.

Another important factor for consideration in sensors, especially metal-oxide based sensors, is humidity dependence. It is well known that metal oxide gas sensors show drift and aging when exposed to varying levels of humidity. Metal oxynitrides, nitrides, oxycarbides, and carbides have less humidity dependence when compared with their analogous oxides. The utilization of these materials will reduce the humidity dependence of the gas sensor.

Embodiments of the present invention use metal oxynitrides, nitrides, oxycarbides or carbides as an etch-resistant material for application as the active sensing materials within a gas sensor for chemically-reactive, noxious analytes. The electronic conductivity of the oxynitride and nitride materials may be tuned via deposition and post-processing for response to a given analyte.

Figure 2:
FIG. 2 is a micrograph of irreversible sensor damage as a result of hydrazine etching.
Figure 3A:
FIGS. 3A-3D illustrate a process for making an etch resistant gas sensor in accordance with embodiments of the present invention.
Figure 3B:
Figure 3C:
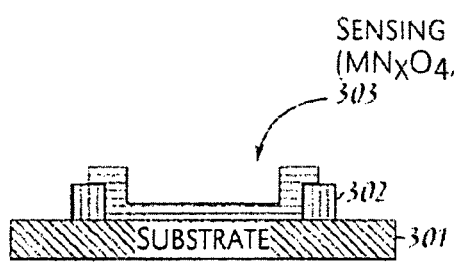
Figure 3D:

One embodiment of a sensor for hydrazine uses both niobium (V) oxide ($Nb_2O_5$) and tungsten (VI) oxide ($WO_3$). These sensors experienced unsatisfactory performances. The niobium (V) oxide was limited in the electronic conductivity achieved through post-processing conditions. The tungsten (VI) oxide was able to achieve a good conductivity and showed excellent response to 3 ppm hydrazine (see FIG. 1). However, this sensor possessed an inability to recover its original electronic conductivity value after its exposure to the hydrazine. This is due to the highly reactive nature of hydrazine and its ability to etch the material. FIG. 2 shows a micrograph of an exemplary sensor after exposure to hydrazine and the amount of material that was etched.

FIGS. 3A-3D illustrate a method for making an etch resistant sensor according to embodiments of the present invention. The sensor may include a substrate 301. The substrate 301 may be insulating, such as silicon nitride. Alternatively, an insulating layer (not shown) may be on top of a conductive substrate or conductive trace on top of the substrate 301. The use of a conductive substrate allows the sensor to be operated using a field-effect mode to further tune sensor response and eliminate, heat. In step 1, photolithographic techniques may be used to pattern metal electrical contacts 302. Examples of such metals are copper, silver, gold or platinum. Following the contact 302 deposition, the sensor material may be applied in step 2, again using photolithography. The sensing material may be comprised of a metal oxide, metal oxynitride, metal oxycarbide or metal carbide. Such metals may be transition metals. The sensor material may be applied using electron-beam evaporation, ion gas sputtering, thermal evaporation, pulsed-laser deposition (PLD), or chemical vapor deposition (CVD). After completion of the sensor material deposition, post-deposition treatments may be performed in step 3. The post-deposition treatments of step 3 may include a thermal anneal while controlling the atmosphere, temperature, time and the heating and cooling rates. The controlled atmosphere may be used to convert a deposited oxide to an oxynitride. For example, niobium oxide may be heated in the presence of ammonia to create niobium oxynitride (see Brayner et. al., "Hydrazine decomposition over niobium oxynitride with macropores generation," Catalysis Today 57 (2000), pp. 225-229). In another example, a deposited oxide can be converted to a carbide such as when molybdenum oxide was heated in the presence of methane to create molybdenum carbide. (See Chen et al., "A novel catalyst for hydrazine decomposition: molybdenum carbide supported on $\gamma$-$Al_2O_3$," Chemical Communications 3 (2002), pp. 288-289.) Controlling the post-deposition conditions will enable tuning of the crystallographic phase or polymorph, surface morphology, compound stoichiometry and therefore sensor response.

In an exemplary embodiment of the present invention, a precursor metal oxide is deposited using electron beam evaporation to a thickness between 75 and 6000 Å onto a substrate pre-patterned with photoresist. A lift-off technique is used to retain the sensing structure on top of predeposited electrodes. The sensing material is then heated in a nitrogen gas or gas used as a source of nitrogen, such as ammonia or hydrazine.

In one embodiment, the sensor material is generated from the metal oxide precursor containing tungsten, molybdenum, indium, niobium, or cobalt. The metal oxides are converted to oxynitrides by annealing in a reactive gas containing nitrogen. The reactive gas may be ammonia with a concentration between 250 ppm and 100% (anhydrous). The crystal structure of the precursor metal oxide dictates the concentration. For example, the two-dimensional layered structure of $\alpha$-$MoO_3$ uses a lower ammonia concentration compared with the three-dimensional structure of $Nb_2O_5$.

In one embodiment, the material is heated in the reactive gas environment to incorporate nitrogen into the crystal lattice of the metal oxide and thus generate the metal oxynitride. These reactions may be performed at temperature less than 375° C. The thickness of the material may determine the reaction temperature. A thin material may require a lower annealing temperature compared with a thick material. The thickness of the material also determines the time of reaction. A thick material requires a longer anneal time compared with a thin material. In this embodiment, a 6000 Å thick $\alpha$-$MoO_3$ layer uses greater than 300° C. for 12 hours compared with a 420 Å thick $\alpha$-$MoO_3$ layer that has a conversion temperature of less than 300° C. for 4 hours.

In one embodiment, the metal oxide precursor is tungsten oxide. In this embodiment, $WO_3$ is deposited onto a substrate between a thickness of 200 Å and 600 Å, and the tungsten oxide thickness is approximately 400 Å. The $WO_3$ is annealed in an ammonia-containing atmosphere to nitridate the material from $WO_3$ to tungsten oxynitride ($WO_xN_y$) where x and y represent the stoichiometric ratios of oxygen and nitrogen, respectively.

Figure 7:
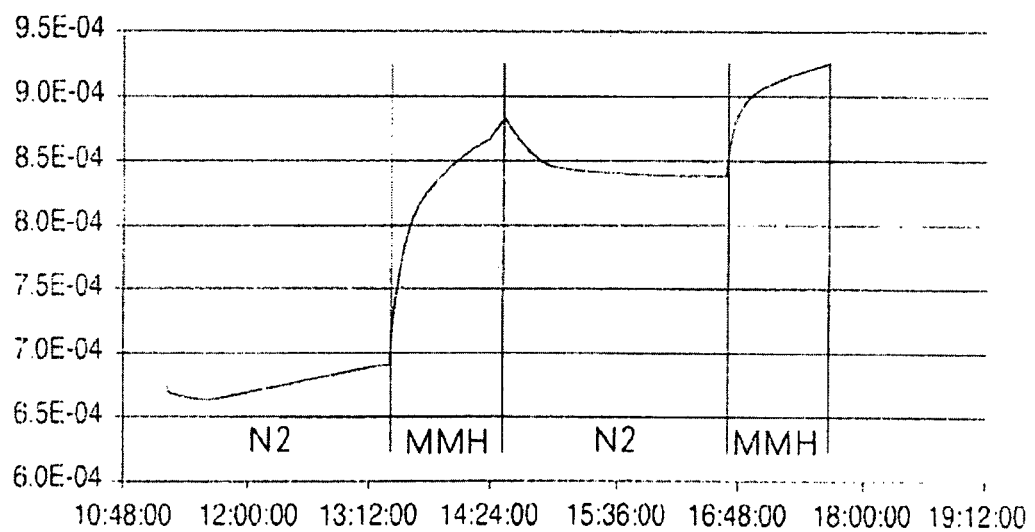
FIG. 7 shows a graph of change in conductivity through exposure to mono-methyl hydrazine.

In one embodiment, the metal oxide is converted to the oxynitride in the presence of hydrazine. The metal oxide sample is placed in a sealed chamber and exposed to hydrazine for a period of time between 2 and 6 hours. As shown in FIG. 7, the conductivity of the material may change up to several orders of magnitude. In this example, indium oxide is converted to indium nitride, and the electronic conductivity increases.

Figure 4:
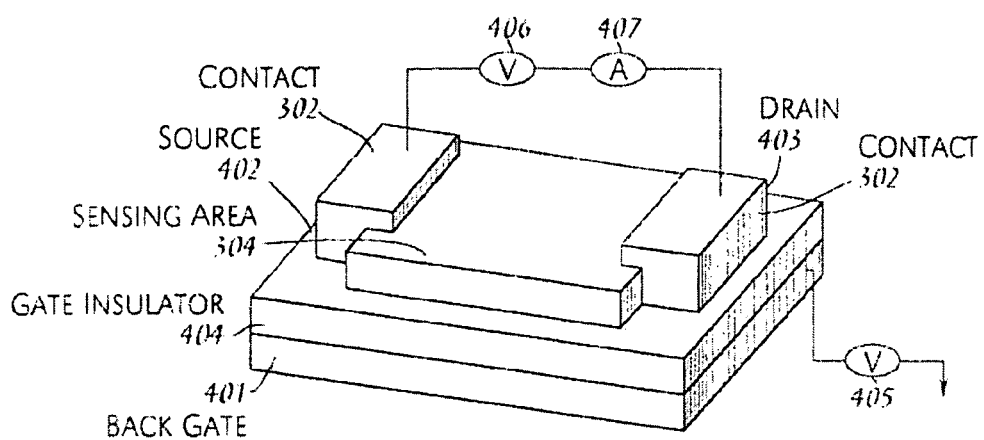
FIG. 4 illustrates a gas sensor configured in accordance with embodiments of the present invention.

In one embodiment, the sensing material (nitride, oxynitride, carbide, or oxycarbide) is incorporated into a thin-film transistor architecture as illustrated in FIG. 4. The sensor contains source 402 and drain 403 electrodes, fashioned from the conductive contacts 302. The sensor material 304 bridges the gap between the source 402 and drain 403 electrodes. The electrodes 402, 403 may contain an interdigitated array (not shown) to increase surface area. A conductive silicon substrate 401 (wafer) serves as a back gate electrode. The source 402 and drain 403 electrodes and the sensor material 304 are separated using a gate dielectric layer 404. This dielectric layer 404 may be silicon nitride, silicon oxide or an equivalent dielectric layer. Application of an applied gate voltage 405 changes the sensitivity of the device. A voltage meter 406 or current meter 407 may be used as an output device for measuring changes in conductivity, which can be measured as a change in resistance, change in current, change in capacitance, or change in impedance, all of which are within the scope of the present invention. A change in resistance or current may be indicated by a DC signal; changes in capacitance or impedance may be indicated by an AC signal.

In one embodiment, the current through the sensor is measured 407 while exposing the sensor to the analyte gas. A voltage is applied across the two metal contact pads 402, 403 and the resulting current is measured. Depending on the material, the current could range from values of $10^{-11}$ to $10^{-3}$ A, or ranges outside of these values. The current will change as the analyte gas is delivered to the sensor.

Figure 5:
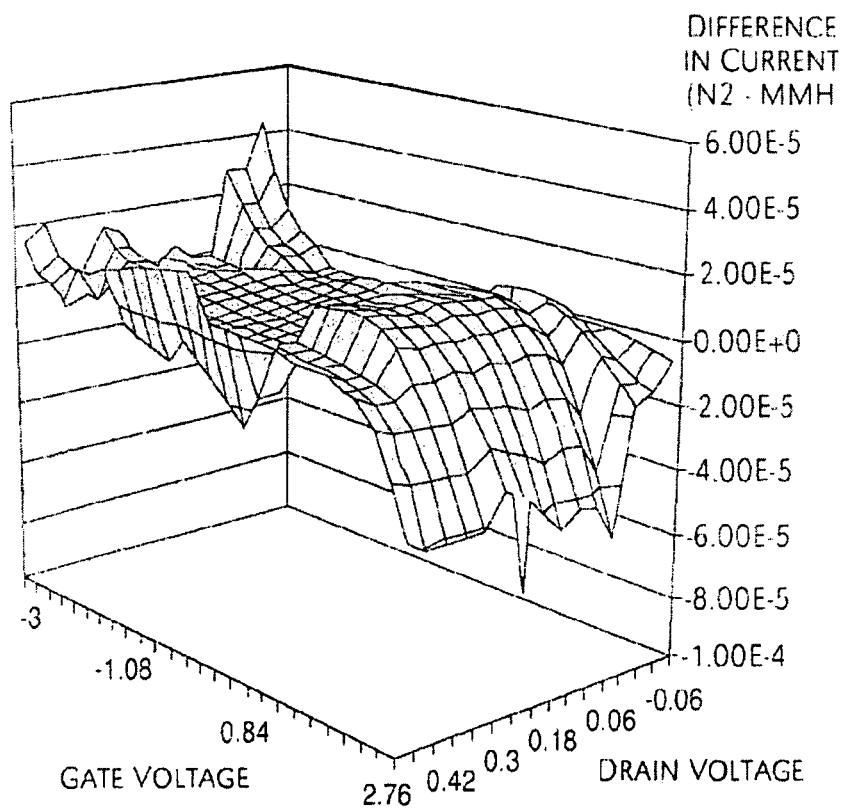
FIG. 5 is a graph of a gate dependent response to monomethyl hydrazine.

In one, embodiment, the current of the device across the source 402 and drain 403 electrodes is measured while sweeping the gate voltage from +3 $V_{gs}$ to −3 $V_{gs}$. In another embodiment, the drain voltage is swept from −0.5 $V_{ds}$ to +0.5 $V_{ds}$. The data creates a "surface plot" matrix that shows the electrical performance of the device. This "surface plot" is created in a background gas such as air or nitrogen. A second "surface plot" is taken while exposing the sensor to the analyte gas. In this embodiment, the background gas is nitrogen and the analyte gas is mono-methyl hydrazine (MMH). The two surface plots are subtracted from one another. The resulting plot shows the difference in current from the resulting exposure of the sensor to the analyte. The plot then shows the optimal gate and drain voltages for maximum sensitivity to the analyte. FIG. 5 shows a surface plot of a $MoO_xN_y$ sample exposed to MMH. Most of the surface shows a difference in current around zero on the vertical z-axis indicating a non-response of the sensor. As the gate voltage is increased above +1.8 $V_{gs}$, the response of the sensor increases. This is shown by the downward fall of the "surface plot." Maximum response of the sensor occurs at about +3 $V_{gs}$. This plot indicates optimal operational conditions for the sensor.

Figure 6:
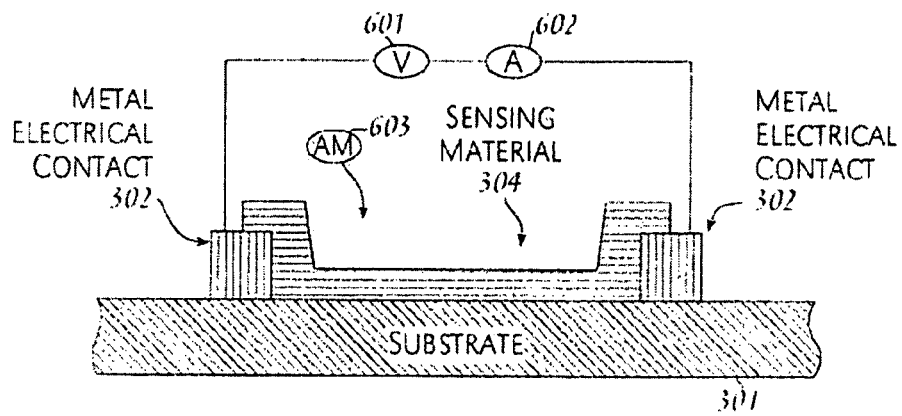
FIG. 6 illustrates a gas sensor configured in accordance with embodiments of the present invention.

FIG. 6 illustrates an alternative sensor configuration. The connections 302 permit measurement equipment such as a voltage source 601, voltage meter 601, current source or current meter 602 to monitor the sensor conductivity. The sensor operates when an analyte molecule (AM) 603 attaches itself to the surface of the sensing material 304. Where, the analyte molecule 603 attaches itself a chemical reaction occurs which results in a transformation of the molecule. For example, in the presence of oxygen, hydrazine breaks down into nitrogen and hydrogen in the following reaction:

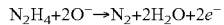

$$N_2H_4 + 2O^- \rightarrow N_2 + 2H_2O + 2e^-$$

The two electrons that remain after the reaction are now read by the measurement equipment 601, 602 as a change in conductivity. The magnitude of response is proportional to the amount of analyte 603 present. Similar reactions may happen with other analytes 603. The conductivity may increase or decrease depending on the type of material and the particular analyte 603 that is reacting. It is possible to distinguish between different molecules 603 by noting the direction of conductivity change. Distinguishing between two analyte molecules may be accomplished by changing the direction and magnitude of the gate voltage. Moreover, it is possible to apply the gate voltage to compensate for device baseline drift and maximize the output stability. And, it is possible to apply the gate voltage to change the sensitivity of the sensor to a specific analyte and also to change the rate of recovery to the sensor.

In an embodiment, the sensor material is sensitive to the analyte MMH. In this embodiment, the sensing material is $WO_xN_y$. The sensing material is a reactive surface that shows a change in conductivity to MMH but not to ammonia. The difference in response is based upon the surface energy level of the sensing material and the reactivity of the analyte.

What is claimed is:

1. A sensor comprising:
   a chemically resistant substrate;
   two electrical contact pads; and
   an etch-resistant sensing material over the substrate, the etch-resistant sensing material connecting the two electrical contact pads, wherein the etch-resistant sensing material is configured to change its conductivity upon exposure to a noxious chemical gas.

2. The sensor according to claim 1, wherein the substrate is covered with silicon nitride.

3. The sensor according to claim 1 wherein the sensor is configured to operate as a chemically sensitive resistor.

4. The sensor according to claim 1, wherein the sensing material is a metal oxynitride.

5. The sensor according to claim 1, wherein the sensing material is a metal nitride.

6. The sensor according to claim 1, wherein the sensing material is a metal oxycarbide.

7. The sensor according to claim 1, wherein the sensing material is a metal carbide.

8. The sensor according to claim 1, wherein the sensing material is selected from the group consisting of indium, molybdenum, tungsten, niobium, cobalt, and combinations thereof.

9. The sensor according to claim 1, wherein the noxious chemical gas is an acid.

10. The sensor according to claim 1, wherein the noxious chemical gas is a base.

11. The sensor according to claim 1, wherein the noxious chemical gas comprises hydrazine.

12. The sensor according to claim 1, wherein the noxious chemical gas comprises a substituted derivative of hydrazine.

13. The sensor according to claim 1, wherein the noxious chemical gas comprises mono-methyl hydrazine.

14. The sensor according to claim 1, wherein the noxious chemical gas comprises dimethyl hydrazine.

15. The sensor according to claim 1, wherein the noxious chemical gas is hydrazine.

16. The sensor according to claim 1, wherein the noxious chemical gas is an oxide of nitrogen.

17. The sensor according to claim 16, wherein the noxious chemical gas is selected from the group consisting of NO, $NO_2$, $N_2O$, and $N_2O_4$.

18. The sensor according to claim 1, wherein the noxious chemical gas is ammonia.

19. The sensor according the claim 1, further comprising source and drain electrodes deposited on the substrate and connected to the sensing material, and a third gate electrode separated from the source, drain and sensing material by a dielectric material.

20. The sensor according to claim 19, wherein the conductive substrate serves as a gate contact to apply a field effect.

21. The sensor according to claim 1, wherein the sensing material is selected from the group consisting of indium, niobium, cobalt, and combinations thereof.

* * * * *